United States Patent [19]

Ison

[11] Patent Number: Plant 7,268

[45] Date of Patent: Jul. 10, 1990

[54] JANEBELL

[76] Inventor: William G. Ison, Rte. 1, Box 19, Hwy. 19, Brooks, Ga. 30205

[21] Appl. No.: 166,247

[22] Filed: Mar. 10, 1988

[51] Int. Cl.[5] ..... A01H 5/00

[52] U.S. Cl. ..... Plt./47

[58] Field of Search ..... Plt./47

*Primary Examiner*—Robert E. Bagwill

*Attorney, Agent, or Firm*—Eugene T. Holmes

[57] ABSTRACT

A cross between the female variety Fry and the pollen parent variety Senoia to produce an improved variety of self-fertile muscadine grape.

1 Drawing Sheet

DESCRIPTION OF THE VARIETY

A cross between the variety seed parent Fry and the pollen parent variety Senoia.

The primary objective of the breeding was to produce an improved variety of muscadine grape; the fruit of which would have superior characteristics for fresh fruit, high quality, 100% dry scar for longer shelf life; for high sugar content; for wine purposes; and the plant to be vigorous and productive.

In comparison with both the seed parent and the pollen parent, the new variety is similar in flavor to the pollen parent. The new variety is similar in color, size and sugar content to the seed parent. This variety contains an average of 22% solid solubles which is higher than the pollen parent. An outstanding characteristic of this new variety is that it has long, vigorous stems growing long clusters of large berries, with anywhere from 8 to 26 berries per cluster. The new variety grows buckshot grapes comparable to the pollen parent. This variety yields anywhere from 6 to 8 tons per acre in tests conducted at Ison's Nursery & Vineyards, Brooks, Ga.

Asexual reproduction of the new variety either by soft-wood cuttings or by layering as performed at Brooks, Ga. shows that the foregoing characteristics and distinctions come true to form and are established and transmitted through succeeding propagations.

The accompanying photograph shows a typical specimen of the vegetative growth and fruit of the new variety when the fruit is ripe and ready for picking and as depicted in color as nearly true as it is reasonably possible to make the same in color illustration of the characters.

The following is a detailed description of the new variety:

Species: *Vitis rotundifolia.*

Type: Vine.

Seed Parent: Variety Fry.

Pollen Parent: Variety Senoia.

Propagation: Holds its characteristics through succeeding propagation by either layering or by soft-wood cuttings.

Locality where grown: Brooks, Ga.

Fruit color: Greyed Yellow Group 161 C Fan 4 Royal Horticultural Society, London, England.

Sugar content: Average 22% Soluble Solids.

Fruit shape: Round.

Seed: Average diameter ⅛ inch, average seed per berry 2.65.

Pulp: A. Color group Greyed Green 195C Fan 4 Royal Horticultural Society London, England. B. Pulp consistency, medium soft, tender, juicy as compared to most muscadine varieties.

Skin: Medium.

Foliage: Leaf color, Group Green, 138B Fan 3 Royal Horticulatural Society, London, England. Leaf size and shape similar to most muscadine varieties.

Productive growth habits: Vine requires support, vigorous and productive.

Reproductive organs: Self-fertile.

Canes: Medium to large caliper.

Maturity date: Usually ripens about Sept. 15 at Brooks, Ga.

Diseases: Tolerant to diseases, slight susceptibility to Black Rot; "common to the muscadine".

This description was made from a muscadine vine grown at Ison's Nursery & Vineyards, Brooks, Ga.

I claim:

1. The new and distinct variety of grape plant as described and illustrated.

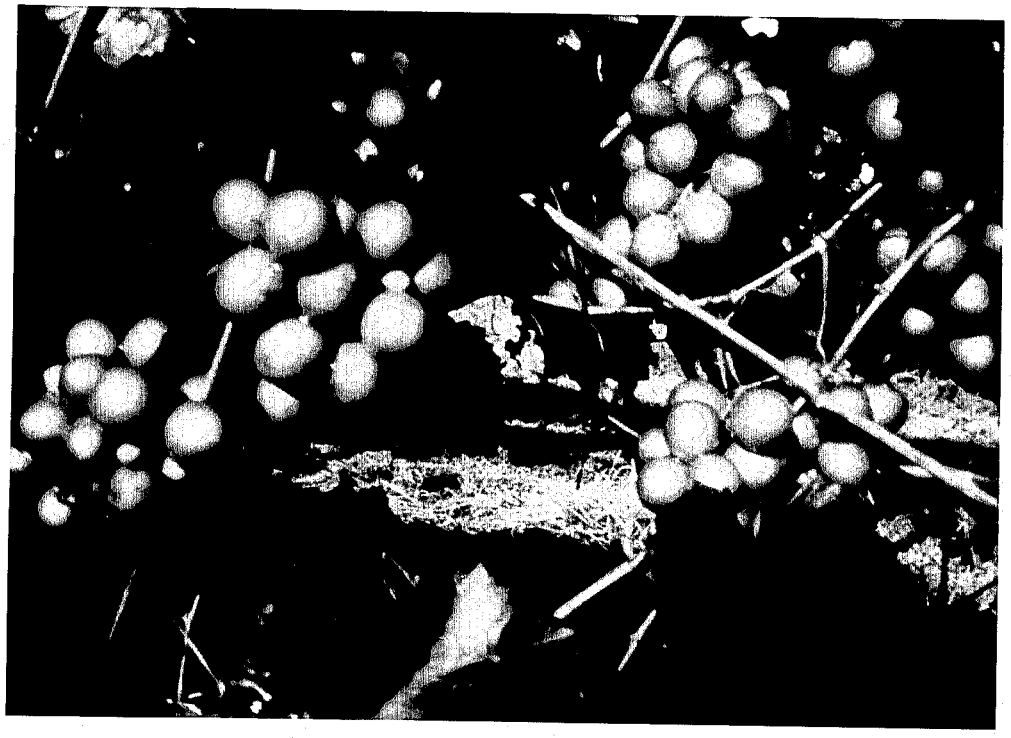

* * * * *